(12) United States Patent
Delprat et al.

(10) Patent No.: US 9,816,064 B2
(45) Date of Patent: Nov. 14, 2017

(54) USE OF A TRANSPARENT COMPOSITION FOR PHOTOBIOREACTORS

(71) Applicant: ARKEMA FRANCE, Colombes (FR)

(72) Inventors: Patrick Delprat, Lescar (FR); Jerome Berge, Parbayse (FR); Jean-Marc Boutillier, Pau (FR)

(73) Assignee: ARKEMA FRANCE, Columbes (FR)

( * ) Notice: Subject to any disclaimer, the term of this patent is extended or adjusted under 35 U.S.C. 154(b) by 0 days.

(21) Appl. No.: 14/851,721

(22) Filed: Sep. 11, 2015

(65) Prior Publication Data

US 2016/0002581 A1  Jan. 7, 2016

Related U.S. Application Data

(63) Continuation of application No. 13/145,442, filed as application No. PCT/FR2010/050095 on Jan. 22, 2010, now abandoned.

(30) Foreign Application Priority Data

Jan. 22, 2009 (FR) .................................... 09 50374
Jul. 17, 2009 (FR) .................................... 09 54969

(51) Int. Cl.
C12M 3/00 (2006.01)
C12M 1/00 (2006.01)

(52) U.S. Cl.
CPC ............ *C12M 21/02* (2013.01); *C12M 23/20* (2013.01); *C12M 23/22* (2013.01); *C12M 39/00* (2013.01); *Y10T 428/1393* (2015.01); *Y10T 428/3154* (2015.04); *Y10T 428/3175* (2015.04); *Y10T 428/31855* (2015.04)

(58) Field of Classification Search
CPC ...... C12M 21/02; C12M 23/20; C12M 39/00; C12M 23/22; Y10T 428/31855; Y10T 428/3154; Y10T 428/1393; Y10T 428/3175

See application file for complete search history.

(56) References Cited

U.S. PATENT DOCUMENTS

| | | | |
|---|---|---|---|
| 4,676,956 A | 6/1987 | Mori | |
| 5,137,828 A | 8/1992 | Robinson | |
| 6,331,584 B1 | 12/2001 | Nodera | |
| 6,370,815 B1 | 4/2002 | Skill | |
| 6,492,149 B1 | 12/2002 | Muller-Feuga | |
| 6,706,851 B1 | 3/2004 | Linemann | |
| 6,784,257 B2 | 8/2004 | Hilgers | |
| 6,913,804 B2 | 7/2005 | Lacroix | |
| 7,056,975 B2 | 6/2006 | Fujimura | |
| 2003/0228684 A1 | 12/2003 | Burbidge | |
| 2004/0197069 A1* | 10/2004 | Mizota et al. | ............ C08F 4/04 385/143 |
| 2005/0064577 A1 | 3/2005 | Berzin | |
| 2007/0048848 A1 | 3/2007 | Sears | |
| 2007/0048859 A1 | 3/2007 | Sears | |
| 2008/0153080 A1 | 6/2008 | Woods | |
| 2010/0099151 A1 | 4/2010 | Stroiazzo-Mougin | |
| 2010/0167381 A1 | 7/2010 | Woerlee | |
| 2011/0117631 A1 | 5/2011 | Woerlee | |
| 2011/0117632 A1 | 5/2011 | Woerlee | |
| 2011/0281340 A1* | 11/2011 | Turner et al. | .......... C12M 21/02 435/257.1 |

FOREIGN PATENT DOCUMENTS

| | | |
|---|---|---|
| FR | 2907311 | 4/2008 |
| JP | 4351547 | 12/1992 |
| JP | 11291415 | 10/1999 |

OTHER PUBLICATIONS

Entire patent prosecution history for U.S. Appl. No. 13/145,442, filed Aug. 29, 2011, entitled "Use of a Transparent Composition for Photobioreactors".

* cited by examiner

*Primary Examiner* — Nathan M Nutter

(74) *Attorney, Agent, or Firm* — RatnerPrestia

(57) ABSTRACT

The present invention relates to photobioreactors and more particularly to the use of a transparent composition based on at least one methacrylic polymer for constructing installations for the culture of photosensitive organisms. This composition can be in the form of films, plates, profiled elements or cylinders such as tubes.

The invention also relates to a transparent multilayer structure comprising at least one layer of a methacrylic polymer and one layer comprising at least one antifouling additive, and to the use thereof for constructing installations for the culture of photosensitive organisms.

15 Claims, 1 Drawing Sheet

US 9,816,064 B2

USE OF A TRANSPARENT COMPOSITION FOR PHOTOBIOREACTORS

CROSS REFERENCE TO RELATED APPLICATIONS

This application is a continuation of U.S. patent application Ser. No. 13/145,442, filed Aug. 29, 2011, which claims priority to International Application No. PCT/FR10/050095, filed Jan. 22, 2010, and French Applications FR 0950374, filed Jan. 22, 2009 and FR 0954969, filed Jul. 17, 2009, the contents of which applications are incorporated by reference herein, in their entireties and for all purposes.

FIELD OF THE INVENTION

The present invention relates to photobioreactors, and the subject thereof is more particularly the use of a transparent composition based on at least one methacrylic polymer for constructing installations for the culturing of photosensitive organisms. This composition can be in the form of films, plates or cylinders such as tubes. A subject of the invention is also a transparent multilayer structure comprising at least one layer of a methacrylic polymer for culturing photosensitive organisms.

BACKGROUND OF THE INVENTION

A photobioreactor is a system in which biological interactions, that it is sought to control by controlling the culturing conditions, take place in the presence of light energy. Within it, a biochemical photosynthesis reaction takes place with the aim of producing plant biomass from photosynthetic microorganisms, light, carbon dioxide gas and a minimum amount of mineral elements. During the mechanism of photosynthesis, most of the organic components are produced (carbohydrates, lipids and proteins).

Microalgae, which are photosynthetic under solar radiation, make it possible, in aquaculture, to produce a biomass of which the composition depends on the species selected, and which can reach, in terms of energy value, according to estimations, twenty to one hundred times that of plants in the ground. There are a few thousand genera of microalgae divided up into species, some of which represent a broad group potentially providing compounds that can be exploited as biofuels or in the cosmetics, pharmacy or even food-processing fields.

Some species are rich in lipids; it is possible to extract the oils (triglycerides) therefrom, giving more or less directly a biofuel. The residues can thus be exploited, for example by fermentation producing bioethanol. Lipid-rich microalgae thus become a technical solution to the energy problems related to the depletion of oil fields and to the replacement of starting materials of fossil origin with renewable materials. Furthermore, the production of algae is accelerated by sparging with $CO_2$ derived, for example, from a polluting industry such as a fuel-burning power station, thus avoiding the immediate discharge of this greenhouse-effect gas. Microalgae also constitute an alternative to the obtaining of biofuels from plant crops (for example rapeseed, beetroot, wheat) which require large cultivatable surface areas. According to American scientists, some microalgae would be capable of synthesizing 30 times more oil per hectare than the terrestrial plants used for the production of biofuels. Moreover, the use of this starting material as a source of biofuels avoids the problems of seasonality and supply which are characteristic of the use of terrestrial plants.

Composed essentially of proteins, some species have a good food precedent since they are rich in vitamins, in polyunsaturated fatty acids and in trace elements. They find applications in agriculture and horticulture through the use of algal extracts which perform not only the role of a fertilizer, but also of a crop accelerator and protector.

Other species represent a productive potential applicable in health fields, for the synthesis of medicaments of biocosmetics from extracts of substances with biological or therapeutic activities, and in the food-processing industry through the extraction and production of pigments, natural dyes or gelling agents. Microalgae can constitute potential sources of molecules that are difficult to obtain by chemical synthesis.

Microalgae can be directly involved in the production of new and renewable energy, in particular the production of biofuels such as hydrogen. Some species can produce hydrogen under the action of the hydrogenase-type enzymes present.

The culture of microalgae offers an advantageous alternative for the treatment of wastewater (municipal, industrial or agricultural effluents). It allows a tertiary biotreatment coupled with the production of potentially exploitable biomass. As a purifying agent, microalgae play various roles such as the simultaneous elimination of nutritive salts ($NH^{4+}$, $NO^{3-}$, $PO_4^{3-}$), the purification of secondary effluents through the production of oxygen which is used by the bacteria to degrade residual organic compounds, or a bactericidal action which reduces the survival of the pathogenic microorganisms contained in the secondary effluents. This technology has the advantage of being based on the principles of natural ecosystems and is therefore not dangerous to the environment.

The growth of microalgae can be carried out at the surface of solar tanks which are open or under greenhouses, which constitutes photobioreactors of limited investment. However, this technology is limited to the use of robust species which can withstand variations in temperature or in sunshine, or viruses. The production of biodiesel from the resulting biomass has not proven to be economically competitive compared with oil products.

For a more stable or more intensive production, closed solar photobioreactors, with transparent walls, are used. This equipment generally has a planar geometry (flat photobioreactors) or a cylindrical geometry (tubular photobioreactors). It is also possible to use photobioreactors with a more particular geometry, such as structures of the "H"-shaped or "I"-shaped hollow profiled element type, for example.

A flat photobioreactor is composed of two transparent parallel panels, of varying surface areas, and between which lies a thin layer of culture which is a few centimeters deep.

A tubular photobioreactor is composed of one or more transparent tubes, of varying diameters and lengths, of various configurations, and within which the culture can circulate. There are many configuration variations:

a wide vertical tube forming a column, two tubes of different diameters arranged one inside the other, forming an annular chamber, a tube placed on the ground and of moderate diameter but of long length, arranged in the form of a coil, a tube of small diameter and of long length coiled helicoidally around a tower, several tubes of small diameter arranged in parallel and vertically.

The particularity of a photobioreactor stems, in addition to the usual needs common to all bioreactors, from the need to supply the microorganisms to be cultured, in particular the microalgae, with a photon energy, this provision being indispensable for the implementation of photosynthesis. From a technological point of view, the chamber of the system must therefore be transparent and be designed so as to supply a sufficient light intensity for the microalgae.

In order to meet this requirement, photobioreactors are generally made of a material which has a high transparency in the visible range, such as glass or polycarbonate (PC).

However, the use of glass, which in addition must be of high purity, has several drawbacks: it is a heavy, expensive, rigid material which breaks easily and which is difficult to machine. Glass also exhibits light scattering which is not as good as methacrylic polymers such as PMMA. Its use limits the choice of the geometry of the reactor: arrangements in the form of loops or coils are difficult to produce, tubes connected to one another by piping or connectors are sources of leakage; in order to maintain correct access of the light, the reactors must be cleaned very frequently owing to the formation of a biofilm on their walls. Optimization between a long tube length, a small surface area on the ground and the accessibility of light to the culture medium proves to be difficult.

Polycarbonate is a product which is not very UV-resistant over time, and the light transmission of which is less than that of PMMA. Moreover, for photobioreactors which require walls of large thickness, PC becomes very fragile. Finally, PC has a low chemical resistance to washing products such as hydrochloric acid, bleach and ozone.

The geometry of the reactor should as far as possible favor a high illuminated surface area to culture volume ratio, while at the same time limiting the ground surface area and remaining appropriate for the objectives of desired biomass concentration and physiological needs of the microorganisms cultured. A hydrodynamic/regulation balance is also to be sought in order to ensure sufficient mixing and a control of the parameters such as consumption of $CO_2$, oxygen given off, or temperature.

In any event, the access to light should be optimized such that the light really available is substantial and uniform within the culture. Different variants are used, for example inclining flat reactors so as to improve the use of solar irradiance, placing the reactors on reflecting surfaces in order to increase radiation incidence by reflection, having artificial light sources in tubes at the heart of the culture medium, etc.

Photobioreactors give rise to many publications; for example, the following documents describe various configurations for carrying out photosynthesis reactions using microorganisms: EP 112 556; EP 239 272; WO 99/20736; WO 00/12673; WO 00/23562; FR 2 907 311; WO 07/025145; WO 08/040828; US 2005/064577.

Regarding the nature of the transparent materials used to produce the culture zones, or reaction tubes or chambers for the microorganism photosynthesis, the prior art proposes various materials among plastics such as polyethylene (PE), polycarbonate (PC), poly(methyl acrylate) (PMA), methacrylic polymers such as poly(methyl methacrylate) (PMMA), cellulose acetate butyrate (CAB), polyvinyl chloride (PVC), polyethylene terephthalate (PET), glycol-modified polyethylene terephthalate (PETG), or nonplastic materials such as glass.

SUMMARY OF THE INVENTION

An object of the present invention is to propose a transparent material capable of replacing glass or polycarbonate for the culture of photosensitive organisms in photobioreactors, which makes it possible to avoid the abovementioned technical problems and drawbacks encountered with the current use of glass or polycarbonate, and makes it possible to improve the efficiency thereof and the lifetime thereof.

The efficiency of the reactor will be all the higher since the material of which it is made will allow light to pass through and this light scattering remains high over time. Moreover, during the cleaning operations, it is necessary to avoid scratching the surface of the reactor and to make sure that the reactor will not crack or break owing to chemical attack of the material by the washing products.

An object of the present invention is to provide a light and easily transportable thermoplastic which is transparent in the visible range (between 400 and 800 nm), which is resistant over time, in particular under the effect of prolonged exposure to sunlight or to moisture, which has a high mechanical strength and good chemical resistance to washing products, and which can be transformed into various forms, that are in particular flexible and connectable.

It has been found, surprisingly, that a methacrylic polymer of PMMA type makes it possible to ally the best performance levels with respect to the plastics PC, PE, PVC and PET, and glass, with the abovementioned aspects, in particular with the following various aspects: transparency, durability in terms of outside exposure, resistance to scratching, chemical resistance, weight and cost.

An objective of the present invention is also to provide transparent films, plates, profiled elements or tubes for constructing installations of various geometries and configurations for the culture of photosensitive organisms.

More precisely, a subject of the present invention is the use of a transparent composition based on at least one methacrylic polymer for constructing installations for the culture of photosensitive organisms, such as photosynthetic bacteria, microalgae or microorganisms, or plankton.

Figure 1:
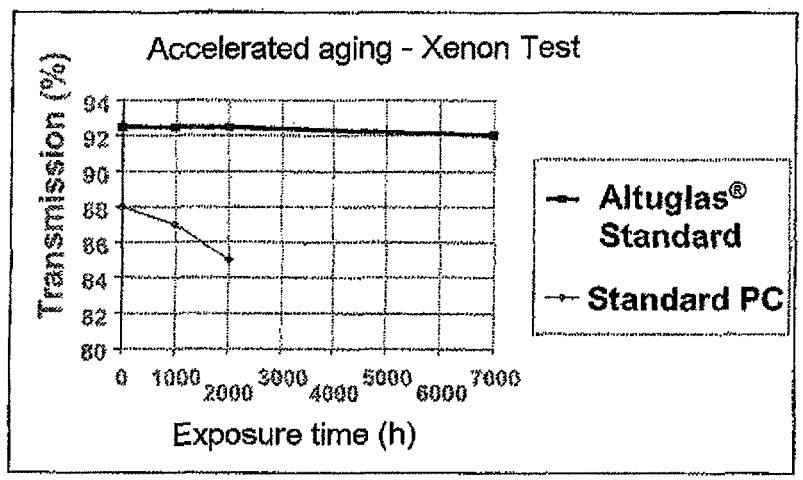
FIG. 1 represents the change in light transmission of the two materials tested as a function of the duration of accelerated aging in a climatic chamber, according to method ISO 4892.

The invention is characterized in that the methacrylic polymer is PMMA-homopolymer of methyl methacrylate MMA or a copolymer of methyl methacrylate (MMA), comprising at least 50% by weight of MMA. The copolymer is obtained from MMA and from at least one comonomer that is copolymerizable with MMA. Preferably, the copolymer comprises from 70 to 99.9% by weight, advantageously from 90 to 99.9% by weight, preferably from 95 to 99.9% by weight of MMA for, respectively, from 0.1 to 30% by weight, advantageously from 0.1 to 10% by weight, preferably from 0.1 to 5% by weight of comonomer.

Preferably, the comonomer that is copolymerizable with MMA is a (meth)acrylic monomer or a vinylaromatic monomer such as, for example, styrene or substituted styrenes.

The comonomer may be chosen, for example, from the list of:
acrylic monomers of formula $CH_2=CH-C(=O)-O-R_1$ where $R_1$ denotes a hydrogen atom, or a linear, cyclic or branched $C_1-C_{40}$ alkyl group optionally substituted with a halogen atom, or a hydroxyl, alkoxy, cyano, amino or epoxy group, for instance acrylic acid, methyl acrylate, ethyl acrylate, propyl acrylate, n-butyl acrylate, isobutyl acrylate, tert-butyl acrylate, 2-ethylhexyl acrylate, glycidyl acrylate, hydroxyalkyl acrylates or acrylonitrile;

methacrylic monomers of formula $CH_2=C(CH_3)-C(=O)-O-R_2$ where $R_2$ denotes a hydrogen atom, or a linear, cyclic or branched $C_2$-$C_{40}$ alkyl group optionally substituted with a halogen atom, or a hydroxyl, alkoxy, cyano, amino or epoxy group, for instance methacrylic acid, methyl methacrylate, ethyl methacrylate, propyl methacrylate, n-butyl methacrylate, isobutyl methacrylate, tert-butyl methacrylate, 2-ethylhexyl methacrylate, glycidyl methacrylate, hydroxyalkyl methacrylates or methacrylonitrile;

vinylaromatic monomers, for instance styrene, substituted styrenes, alpha-methylstyrene, monochlorostyrene or tert-butyl styrene.

The comonomer may also be a crosslinking agent, i.e. a molecule or an oligomer having at least two ethylenic unsaturations, polymerizable with MMA via a free-radical mechanism. The crosslinking agent may be difunctional. It may, for example, be ethylene glycol di(meth)acrylate, hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, dipropylene glycol di(meth)acrylate, allyl di(meth)acrylate, or divinylbenzene di(meth)acrylate. The crosslinking agent may also be trifunctional. It may, for example, be tripropylene glycol tri(meth)acrylate, trimethylolpropane tri(meth)acrylate or pentaerythrityl tri(meth)acrylate. The crosslinking agent may also be tetrafunctional, for instance pentaerythrityl tetra(meth)acrylate, or hexafunctional such as dipentaerythrityl hexa(meth)acrylate.

Preferably, the comonomer is an alkyl(meth)acrylate, in particular methyl acrylate, ethyl acrylate, propyl acrylate, butyl acrylate or butyl methacrylate.

The PMMA may advantageously be a copolymer of MMA and of acrylic and/or methacrylic acid. This type of PMMA offers thermomechanical resistance and also improved resistance to scratching compared with a PMMA which does not contain said acrylic and/or methacrylic acid.

The PMMA exhibits light transmission characteristics which are superior to those of the other transparent polymers and of glass, as shown in the table hereinafter:

|  | Transmission, %<br>Standard ASTM D1003 |
| --- | --- |
| PMMA Standard | 92 |
| PMMA impact | 90-92 |
| Glass | 90 |
| PC | 84-88 |
| SAN | 84-89 |
| ABS Transparent | 80-89 |
| PA | 86 |
| PS | 89 |
| Copolyesters and PET | 82-91 |

The PMMA exhibits scratch resistance properties which are superior to those of the other transparent polymers, as indicated in the table hereinafter:

|  | Pencil test*<br>Standard ASTM D3363 |
| --- | --- |
| PMMA Standard | 2H-4H |
| PMMA Impact | B-2H |
| PC | 3B-HB |
| SAN, ABS Transparent, PA, PS, PVC, PET, PA, | <B |

Figure 2:
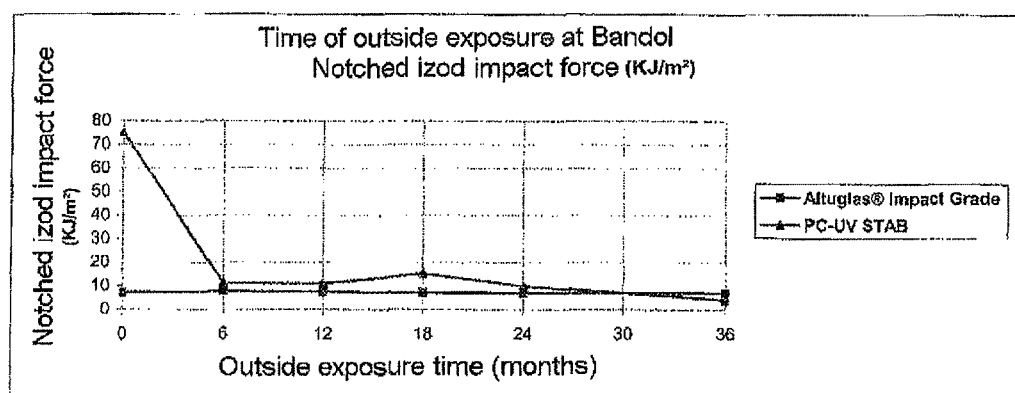
FIG. 2 illustrates the loss of mechanical properties of PC after 6 months of outside exposure, according to method NF T51-165.

*Hardness of the leads available (from the softest to the hardest): 7B-6B-5B-4B-3B-2B-B-HB-F-H-2H-3H-4H-5H-6H In addition, FIGS. 1 and 2 illustrate the superior properties of PMMA (standard grade) compared with a standard polycarbonate PC, in terms of durability with respect to outside exposure and UV resistance.

FIG. 1 represents the change in light transmission of the two materials tested as a function of the duration of accelerated aging in a climatic chamber, according to method ISO 4892. FIG. 2 illustrates the loss of mechanical properties of PC after 6 months of outside exposure, according to method NF T51-165.

The methacrylic polymer according to the invention has a weight-average molecular weight ($M_w$) ranging from 90 000 g/mol to 170 000 g/mol, advantageously from 110 000 g/mol to 170 000 g/mol, preferably from 140 000 g/mol to 160 000 g/mol (PMMA equivalent standard calculated on the basis of the PS standard). According to the invention, the weight-average molecular weight is determined according to the method by gel permeation chromatography (GPC), also called size exclusion chromatography (SEC). Operating conditions that can be used to implement this method are the following: The samples are prepared at a concentration of 1 g/l, with a dissolving time of a minimum of 4 hours. The measuring conditions are the following: solvent: THF; temperature: 30° C.; injected volume: 100 µl; detection: refractive index; calibration with polystyrene (PS) standards using the universal calibration. The weights are expressed in PMMA equivalent by virtue of the Mark-Houwink-Sakurada coefficients. An instrument from the company Waters (Milford USA) can, for example, be used for this determination.

Chemical resistance tests (according to method EN 13559) have in fact shown, surprisingly, that PMMAs having a molecular weight of less than 90 000 g/mol do not make it possible to withstand the products used for cleaning the photobioreactors. Moreover, PMMAs having a molecular weight of less than 90 000 g/mol prove to be fragile in a hot humid chamber (85% humidity and temperature of 85° C.), and are not therefore suitable for the use envisioned.

The methacrylic polymers sold under the trademark Altuglas®, in particular grade HCR-3, are perfectly suitable for the invention.

The composition based on at least one methacrylic polymer according to the invention may be impact-strengthened by means of at least one impact modifier. An extruder is advantageously used to prepare the mixture. The impact modifier may, for example, be an acrylic elastomer. The acrylic elastomer may be a block copolymer having at least one elastomeric block. For example, it may be a styrene-butadiene-methyl methacrylate or methyl methacrylate-butyl acrylate-methyl methacrylate copolymer. The impact modifier may also be in the form of fine multilayer particles, called core-shell particles, having at least one elastomeric (or soft) layer, i.e. a layer made up of a polymer having a $T_g$ below −5° C., and at least one rigid (or hard) layer, i.e. made up of a polymer having a $T_g$ above 25° C.

The composition according to the invention may also comprise conventionally used additives, chosen from thermal stabilizers, for example di-tert-dodecyl disulfide (DtDDS) or Irganox© 1076; lubricants, for example stearic acid or stearyl alcohol; fire retardants, for example antimony trioxide or a brominated or chlorinated phosphate ester; organic or inorganic pigments; anti-UV agents, for example Tinuvin© P; antioxidants, such as hindered phenol compounds; and antistatic agents.

Advantageously, the composition according to the invention comprises at least one antifouling and/or antistatic additive in order to avoid phenomena of attachment and fouling in the presence of the culture medium and/or in the presence of air. The use of such additives to the methacrylic composition also makes it possible to use concentrated culture media without the emergence of problems of attachment of the photosensitive organisms to the walls in contact with the organic medium and/or in contact with the air.

As antifouling and/or antistatic additive, use may in particular be made of a copolymer comprising polyamide and polyether blocks (also called PEBA according to the IUPAC).

PEBAs or polyether-block-amides, such as those sold by the company Arkema under the name Pebax®, result from the polycondensation of polyamide blocks PA comprising reactive end groups with polyether blocks PE comprising reactive end groups, such as, inter alia:
1) polyamide blocks comprising diamine chain ends with polyoxyalkylene blocks comprising dicarboxylic chain ends;
2) polyamide blocks comprising dicarboxylic chain ends with polyoxyalkylene blocks comprising diamine chain ends, obtained by cyanoethylation and hydrogenation of alpha,omega-dihydroxylated aliphatic polyoxyalkylene blocks called polyetherdiols;
3) polyamide blocks comprising dicarboxylic chain ends with polyetherdiols, the products obtained being, in this particular case, polyetheresteramides.

The polyamide blocks comprising dicarboxylic chain ends originate, for example, from the condensation of polyamide precursors in the presence of a chain-limiting dicarboxylic acid.

The polyamide blocks comprising diamine chain ends originate, for example, from the condensation of polyamide precursors in the presence of a chain-limiting diamine.

The number-average molar mass Mn of the polyamide blocks is included in the range of from 400 to 20 000 g/mol, preferably from 500 to 10 000 g/mol, and more preferably from 600 to 6000 g/mol.

The polymers comprising polyamide blocks and polyether blocks can also comprise randomly distributed units.

The polyamide blocks can comprise homopolyamides or copolyamides.

Three types of polyamides can be part of the composition of these PA blocks. According to a first type, the polyamide blocks originate from the condensation of at least one (aliphatic, cycloaliphatic or aromatic) dicarboxylic acid, in particular those having from 4 to 36 carbon atoms, preferably those having from 6 to 18 carbon atoms, and of at least one (aliphatic, cycloaliphatic or aromatic) diamine chosen in particular from those having from 2 to 20 carbon atoms, preferably those having from 6 to 15 carbon atoms.

By way of examples of aliphatic diacids, mention may be made of butanedioic acid, adipic acid, suberic acid, azelaic acid, sebacic acid, dodecanedicarboxylic acid, myristic acid, tetradecanedicarboxylic acid, hexadecanedicarboxylic acid, octadecanedicarboxylic acid and dimerized fatty acids.

By way of examples of cycloaliphatic diacids, mention may be made of 1,4-cyclohexyldicarboxylic acid.

By way of examples of aromatic diacids, mention may be made of terephthalic acid (T) and isophthalic acid (I).

By way of examples of aliphatic diamines, mention may be made of tetramethylenediamine, hexamethylenediamine, 1,10-decamethylenediamine, dodecamethylenediamine and trimethylhexamethylenediamine.

By way of example of cycloaliphatic diamines, mention may be made of the isomers of bis(4-aminocyclohexyl) methane (BACM or PACM), bis(3-methyl-4-aminocyclohexyl)methane (BMACM or MACM) and 2-2-bis(3-methyl-4-aminocyclohexyl)propane (BMACP), isophoronediamine (IPDA), 2,6-bis(aminomethyl)norbornane (BAMN) and piperazine (Pip).

Advantageously, the copolymer comprises at least one PA block based on PA 4.4, PA 4.6, PA 4.9, PA 4.10, PA 4.12, PA 4.14, PA 4.16, PA 4.18, PA 4.36, PA 6.4, PA 6.6, PA 6.9, PA 6.10, PA 6.12, PA 6.13, PA 6.14, PA 6.16, PA 6.18, PA 6.36, PA 9.4, PA 9.6, PA 9.10, PA 9.12, PA 9.14, PA 9.18, PA 9.36, PA 10.4, PA 10.6, PA 10.9, PA 10.10, PA 10.12, PA 10.13, PA 10.14, PA 10.16, PA 10.18, PA 10.36, PA 10.T, PA BMACM.4, PA BMACM.6, PA BMACM.9, PA BMACM.10, PA BMACM.12, PA BMACM.14, PA BMACM.16, PA BMACM.18, PA BMACM.36, PA PACM.4, PA PACM.6, PA PACM.9, PA PACM.10, PA PACM.12, PA PACM.14, PA PACM.16, PA PACM.18, PA PACM.36, PA Pip.4, PA Pip.6, PA Pip.9, PA Pip.10, PA Pip.12, PA Pip.14, PA Pip.16, PA Pip.18 and/or PA Pip.36, and mixtures thereof.

According to a second type, the polyamide blocks result from the condensation of one or more alpha, omega-aminocarboxylic acids and/or of one or ore lactams having from 6 to 12 carbon atoms in the presence of a dicarboxylic acid having from 4 to 12 carbon atoms or of a diamine.

By way of examples of lactams, mention may be made of caprolactam, enantholactam and lauryllactam.

By way of examples of alpha, omega-aminocarboxylic acids, mention may be made of aminocaproic acid, 7-aminoheptanoic acid, 11-aminoundecanoic acid and 12-aminododecanoic acid.

The dicarboxylic acids or the diamines may be chosen from those mentioned above.

Advantageously, the polyamide blocks of the second type are of polyamide 11, of polyamide 12 or of polyamide 6.

According to a third type, the polyamide blocks result from the condensation of at least one monomer of the first type with at least one monomer of the second type. In other words, the polyamide blocks result from the condensation of at least one alpha, omega-aminocarboxylic acid (or one lactam), with at least one diamine and one dicarboxylic acid.

In this case, the PA blocks are prepared by polycondensation:
of the aliphatic, cycloaliphatic or aromatic diamine(s) having X carbon atoms;
of the dicarboxylic acid(s) having Y carbon atoms; and
of the comonomer(s) {Z}, chosen from lactams and alpha, omega-aminocarboxylic acids having Z carbon atoms;
in the presence of a chain limiter chosen from dicarboxylic acids or diamines or of an excess of diacid or of diamine used as structural unit.

Advantageously, the dicarboxylic acid having Y carbon atoms is used as chain limiter, and is introduced in excess with respect to the stoichiometry of the diamine(s).

According to another variant (the case of the copolymers, i.e. copolyamides), the polyamide blocks result from the condensation of at least two different alpha, omega-aminocarboxylic acids or of at least two different lactams having from 6 to 12 carbon atoms or of one lactam and one aminocarboxylic acid not having the same number of carbon atoms, optionally in the presence of a chain limiter.

By way of examples of polyimide blocks of the third type, mention may be made of those made up of the following polyamides (copolyamides):

PA 6/6.6 in which 6 denotes caprolactam and 6.6 denotes a monomer resulting from the condensation of hexamethylenediamine with adipic acid.

PA 6.6/Pip.10/12 in which 6.6 denotes a monomer resulting from the condensation of hexamethylenediamine with adipic acid, Pip.10 denotes a monomer resulting from the condensation of piperazine with sebacic acid, and 12 denotes lauryllactam.

PA 6.6/6.10/11/12 in which 6.6 denotes a monomer resulting from the condensation of hexamethylenediamine with adipic acid, 6.10 denotes a monomer resulting from the condensation of hexamethylenediamine with sebacic acid, 11 denotes 11-aminoundecanoic acid, and 12 denotes lauryllactam.

By way of examples, mention may be made of PA 10.10/11, PA 6.10/11, PA10.12/11, PA 10.10/11/12, PA 6.10/10.10/11, PA 6.10/6.12/11, and PA 6.10/6.12/10.10.

In PEBAs, the polyether blocks can represent 1 to 99%, and preferably 5 to 90% by weight of the copolymer comprising polyamide and polyether blocks, even more preferentially from 10 to 50% by weight. The molar mass Mn of the polyether blocks is included in the range of from 100 to 6000 g/mol and preferably from 200 to 3000 g/mol, even more preferentially from 250 to 2000 g/mol.

The term "polyether blocks" (hereinafter abbreviated to PE blocks) is intended to mean polyalkylene ether polyols, in particular polyalkylene ether diols, such as poly(ethylene glycol) (PEG), poly(1,2-propylene glycol) (PPG), polytetramethylene ether glycol (PTMG), polyhexamethylene glycol, poly(1,3-propylene glycol) (PO3G), poly(3-alkyl tetrahydrofuran), in particular poly(3-methyltetrahydrofuran (poly(3MeTHF)), and mixtures thereof. It is also possible to envision a PE block of block or random "copolyether" type containing a sequence of at least two types of PE mentioned above. The polyether blocks may also comprise blocks obtained by oxyethylation of bisphenols, such as, for example, bisphenol A. The latter products are described in patent EP 613 919.

The polyether blocks may also comprise ethoxylated primary amines. These blocks are advantageously also used. By way of example of ethoxylated primary amines, mention may be made of the products of formula:

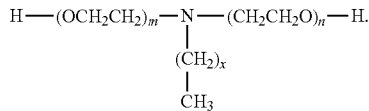

in which m and n are between 1 and 20 and x between 8 and 18. These products are commercially available under the trademark Noramox® from the company Ceca and under the trademark Genamin® from the company Clariant.

Thus, the chain ends of the PE blocks may be diOH, diNH$_2$, diisocyanate or diacid depending on their synthesis process.

The PE blocks comprising NH$_2$ chain ends can be obtained by cyanoacetylation of alpha, omega-dihydroxylated aliphatic polyoxyalkylene blocks called polyetherdiols, such as Jeffamines® D300, D400, D2000, ED-600, ED-900 and ED2003 and Elastamines® RP-409, RP-2009, RT-1000, RE-600, RE-900, RE-2000, HT-1700 and HE-180 from the company Huntsman. Such blocks are described in patents JP 2004346274, JP 2004352794 and EP1482011.

The preparation of the PEBA copolymers comprising polyamide block(s) and polyether block(s) comprises any means for attaching the polyamide blocks (PA block) and the polyether blocks (PE block) according to the present invention. In practice, two processes are essentially used, one termed a two-step process, the other a one-step process.

The general method for the two-step preparation of PEBA copolymers having ester bonds between the PA blocks and the PE blocks is known and is described, for example, in French patent FR 2 846 332. The general method for the preparation of PEBA copolymers having amide bonds between the PA blocks and the PE blocks is known and described, for example, in European patent. EP 1 482 011.

Advantageously, the methods in two steps or in a single step that are described in document WO 01/18111 are used.

According to the invention, the following are advantageously used as antifouling and/or antistatic additives:

copolymers comprising polyamide blocks and polyether blocks which comprise essentially ethylene oxide units and in which the polyamide blocks are copolyamides resulting from the condensation of at least one alpha, omega-aminocarboxylic acid (or one lactam), at least one diamine and at least one dicarboxylic acid, as described in document EP 1 046 675, polyetheresteramides having polyamide blocks comprising dicarboxylic acid sulfonates either as chain limiters of the polyamide block, or associated with a diamine as one of the monomers making up the polyamide block, and having polyether blocks consisting essentially of alkylene oxide units, as described in document WO 01/29113, a mixture of a copolymer comprising polyamide blocks and polyether blocks and of a polymer or oligomer comprising, in its chain, at least one ionic function and chosen from polyamides, copolymers comprising polyamide blocks and polyether blocks, thermoplastic polyesters or polyetheramides, copolymers comprising polyester blocks and polyether blocks, polyethers and polyurethanes, as described in document EP 1 262 527.

According to one preferred embodiment of the invention, copolymers having polyamide 12 blocks and polyether blocks comprising essentially ethylene oxide units are used as antifouling and/or antistatic additives. In particular, the Pebax®MV 1074 having polyamide 12 blocks with a number-average molar mass of 1500 and PEG blocks with a number-average molar mass of 1500.

The antifouling and/or antistatic additives described above are preferably used at a content that can range from 3 to 15% by weight relative to the total composition, i.e. that makes it possible for the material to have a slip effect and not to attract dust. Depending on the content of additive, a methacrylic polymer having antifouling properties or a methacrylic polymer having antistatic properties may be obtained. By way of example, a composition of PMMA comprising from 5% to 10%, more particularly from 6% to 8% of a PEBA results in a composition having good antistatic properties. Preferably, in order to obtain a methacrylic polymer having antifouling properties, the additive will be present at a content ranging from 3% to 7% by weight relative to the total composition.

The antistatic and/or antifouling property of a polymer can be measured by its surface resistivity. By way of example, a film of 500 μm of PMMA alone having a molecular weight equal to 150 000 g/mol has a surface resistivity of 126 $10^{+15}$ Ohms. The addition of 7% by weight and 10% by weight of Pebax® MV 1074 to the PMMA makes it possible, respectively, to obtain surface resistivities, measured on a film of 500 μm, of 136 $10^{+12}$ and 47 $10^{+12}$ Ohms, the surface resistivity measurements having been carried out using a Keithley cell connected to an electrometer, according to standard ASTM D257, with a measuring voltage of 500 volts.

The antifouling property (slip effect) can be quantified by means of measurements of the coefficient of friction according to standard ASTM D1894-08 which makes it possible to determine the force required to cause a sled to slip over the surface of the part to be evaluated. The tests carried out according to this standard give coefficients of static and dynamic friction for a standard Altuglas of V046 type, of 0.154 and 0.107. This grade with 5% of added Pebax MV1074 has values for the coefficients of static and dynamic friction of 0.074 and 0.053.

According to one variant of the invention, a fluoropolymer which makes it possible to provide antifouling properties, but also good resistance, in particular to UV radiation and to chemical products, is used as antifouling additive. Denoted in this way is any polymer having in its chain at least one monomer chosen from compounds containing a vinyl group capable of opening so as to polymerize and which contains, directly attached to this vinyl group, at least one fluorine atom, one fluoroalkyl group or one fluoroalkoxy group.

By way of example of a monomer, mention may be made of vinyl fluoride; vinylidene fluoride (VDF, $CH_2=CF_2$); trifluoroethylene ($VF_3$); chlorotrifluoroethylene (CTFE); 1,2-difluoroethylene; tetrafluoroethylene (TEE); hexafluoropropylene (HFP); perfluoro(alkyl vinyl) ethers such as perfluoro(methyl vinyl) ether (PMVE), perfluoro(ethyl vinyl) ether (PEVE) and perfluoro(propyl vinyl) ether (PPVE); perfluoro(1,3-dioxole); perfluoro(2,2-dimethyl-1,3-dioxole) (PDD); the product of formula $CF_2=CFOCF_2CF(CF_3)OCF_2CF_2X$ in which X is $SO_2F$, $CO_2H$, $CH_2OH$, $CH_2OCN$ or $CH_2OPO_3H$; the product of formula $CF_2=CFOCF_2CF_2SO_2F$; the product of formula $F(CF_2)_nCH_2OCF=CF_2$ in which n is 1, 2, 3, 4 or 5; the product of formula $R_1CH_2OCF=CF_2$ in which $R_1$ is hydrogen or $F(CF_2)z$ and z is 1, 2, 3 or 4; the product of formula $R_3OCF=CH_2$ in which $R_3$ is $F(CF_2)_z$— and z is 1, 2, 3 or 4; perfluorobutylethylene (PFBE); 3,3,3-trifluoropropene and 2-trifluoromethyl-3,3,3-trifluoro-1-propene.

The fluoropolymer may be a fluorinated homopolymer or a fluorinated copolymer that may also comprise nonfluorinated monomers such as ethylene or propylene.

By way of example, the fluoropolymer is chosen from:
homopolymers and copolymers of vinylidene fluoride (VDF, $CH_2=CF_2$) containing at least 50% by weight of VDF. The comonomer of the VDF may be chosen from chlorotrifluoroethylene (CTFE), hexafluoropropylene (HFP), trifluoroethylene ($VF_3$) and tetrafluoroethylene (TFE);
copolymers of TFE and of ethylene (ETFE);
homopolymers and copolymers of trifluoroethylene ($VF_3$);
copolymers of the EFEP type combining VDF and TFE (in particular the EFEPs from Daikin);
copolymers, and in particular terpolymers, combining the residues of chlorotrifluoroethylene (CTFE), tetrafluoroethylene (TFE), hexafluoropropylene (HFP) and/or ethylene units and, optionally, VDF and/or $VF_3$.

Advantageously, the fluoropolymer is a PVDF homopolymer or copolymer. This fluoropolymer in fact exhibits good chemical resistance, in particular to UV radiation and to chemical products, and it is completely miscible in a methacrylic polymer matrix, Preferably, the PVDF contains at least 50% by weight of VDF, more preferentially at least 75% by weight and even better still at least 85% by weight. The comonomer is advantageously HFP.

Thus, the PVDFs sold under the trademark Kynar®, in particular grades 710, 720 or 740, are perfectly suitable for this formulation.

The fluoropolymer is preferably present at a content that can range from 5 to 60% by weight relative to the total composition, preferably from 20 to 40%.

The composition according to the invention can be prepared by the usual techniques of thermoplastics, for instance by extrusion or by means of twin-screw mixers or else by means of an apparatus of the Buss® Ko-kneader type.

The composition according to the invention may be in the form of a powder, of granules or of pellets.

The composition according to the invention may be formed into films, plates, hollow profiled elements which are "H"-shaped or "I"-shaped for example, or cylinders such as tubes, according to conventional extrusion or injection-molding processes.

According to one variant of the invention, the antifouling and/or antistatic additive is used in the form of a layer of small thickness at the surface of the methacrylic polymer.

Thus, the invention also relates to a transparent multilayer structure comprising at least one layer of a methacrylic polymer and one layer comprising at least one antifouling and/or antistatic additive, and also to the use thereof for constructing installations for the culture of photosensitive organisms, such as photosynthetic bacteria, microalgae or microorganisms, or plankton.

Advantageously, the multilayer structure comprises at least:
one layer of at least one methacrylic polymer as defined above,
one layer comprising at least one antifouling additive that may be in contact with a culture medium,
the layers being arranged one on top of the other.

Advantageously, the layer in contact with the culture medium consists either of an antifouling methacrylic polymer defined in the present invention by a methacrylic polymer as defined above, to which has been added at least one antifouling additive chosen from the copolymers comprising polyamide blocks and polyether blocks and the fluoropolymers defined above, or of a polymer having antifouling properties which is chosen from the fluoropolymers defined above.

Preferably, the multilayer structure comprises, in the following order, at least:
one layer comprising at least one antistatic additive that may be in contact with the air or the outside environment,
one layer of at least one methacrylic polymer as defined above,
one layer comprising at least one antifouling additive that may be in contact with a culture medium.

Advantageously, the layer in contact with the air or the outside environment consists of an antistatic methacrylic polymer, defined in the present invention by a methacrylic polymer to which has been added from 5 to 10% of an antistatic additive chosen from copolymers comprising polyamide blocks and polyether blocks.

The monolayer or multilayer structure has a thickness of between 200 μm and 12 mm, preferably between 500 μm and 7 mm.

The antistatic or antifouling layer has a thickness of between 50 μm and 2 mm, and preferably between 100 μm and 1 mm.

The multilayer structures can be coextruded, hot-compressed, coextruded-laminated, and are preferably coextruded, making it possible to obtain multilayer tubes or plates.

The invention also relates to a multilayer tube that can have a diameter of from 2 to 100 cm, preferably from 10 to 60 cm, and a length of from 1 to 50 meters.

The invention also relates to a plate that can have a thickness of from 1 to 100 mm and a width and length of from 1 to 50 meters.

The invention also relates to an installation for culturing photosensitive organisms, comprising transparent films, plates, profiled elements or tubes based on at least one methacyrlic polymer as defined in the invention.

What is claimed is:

1. A photobioreactor for the culture of photosensitive organisms comprising a transparent composition of at least one methacrylic polymer wherein the methacrylic polymer is a copolymer of methyl methacrylate (MMA), comprising from 90 to 99.9% by weight of MMA and from 0.1 to 10% by weight of a comonomer, said methacrylic polymer having a weight-average molecular weight ranging from 140 000 g/mol to 160 000 g/mol (PMMA standard), wherein said composition comprises at least one antifouling and/or antistatic additive.

2. The photobioreactor of claim 1, wherein said antifouling and/or antistatic additive is a copolymer comprising polyamide blocks and polyether blocks that is present at a content ranging from 3% to 15% by weight relative to the total composition.

3. The photobioreactor of claim 1, wherein said antifouling and/or antistatic additive is a fluoropolymer chosen from homopolymers and copolymers of vinylidene fluoride (VDF) containing at least 50% by weight of VDF; copolymers of tetrafluoroethylene and of ethylene (ETFE); homopolymers and copolymers of trifluoroethylene (VF$_3$); copolymers combining VDF and tetrafluoroethylene (EFEP); copolymers, combining the residues of chlorotrifluoroethylene (CTFE), tetrafluoroethylene (TFE), hexafluoropropylene (HFP) and/or ethylene units; terpolymers combining the residues of chlorotrifluoroethylene (CTFE), tetrafluoroethylene (TFE), hexafluoropropylene (HFP) and/or ethylene units and, optionally, VDF and/or VF$_3$ units, the fluoropolymer being present at a content ranging from 5 to 60% by weight relative to the total composition.

4. The photobioreactor of claim 3, wherein said fluoropolymer is a PVDF homopolymer or copolymer containing at least 75% of VDF.

5. The photobioreactor of claim 1, wherein said composition is in the form of films, plates, profiled elements or cylinders.

6. A multilayer structure comprising at least:
one or more transparent composition layers of at least one methacrylic polymer, wherein the methacrylic polymer is a copolymer of methyl methacrylate (MMA), comprising from 90 to 99.9% by weight of MMA and from 0.1 to 10% by weight of a comonomer, wherein the methacrylic polymer having a weight-average molecular weight ranging from 140 000 to 160 000 g/mol (PMMA standard);
one or more antifouling layers comprising at least one antifouling additive, wherein the one or more antifouling layers is in contact with a culture medium; and
wherein the one or more transparent composition layers and the one or more antifouling layers are directly in contact with one another.

7. The multilayer structure as claimed in claim 6, wherein the layer that is in contact with a culture medium consists either of an antifouling methacrylic polymer defined as a methacrylic polymer to which has been added at least one antifouling additive chosen from copolymers comprising polyamide blocks and polyether blocks or fluoropolymers, or an antifouling fluoropolymer.

8. The multilayer structure as claimed in claim 6, comprising, in the following order, at least:
one layer comprising at least one antistatic additive that is in contact with the air or the outside environment,
one layer of at least one methacrylic polymer,
one layer comprising at least one antifouling additive that is in contact with a culture medium.

9. The structure as claimed in claim 8, wherein the layer in contact with the air or the outside environment consists of an antistatic methacrylic polymer, defined as a methacrylic polymer to which has been added from 5 to 10% of an antistatic additive chosen from copolymers comprising polyamide blocks and polyether blocks.

10. The multilayer structure as claimed in claim 6, wherein said structure is in the form of a tube, a profiled element or a plate.

11. The multilayer tube as claimed in claim 10, wherein said tube has a diameter ranging from 2 to 100 cm and a length from 1 to 50 m.

12. The multilayer plate as claimed in claim 10, wherein said plate has a thickness ranging from 1 to 100 mm.

13. The multilayer structure as claimed in claim 6, comprising an installation for the culture of photosensitive organisms.

14. The photobioreactor of claim 1, wherein said photosensitive organisms, are selected from the group consisting of photo synthetic bacteria, microalgae, microorganisms, and plankton.

15. The photobioreactor of claim 13, wherein said photosensitive organisms, are selected from the group consisting of photosynthetic bacteria, microalgae, microorganisms, and plankton.

* * * * *